(12) United States Patent
Ponceblanc et al.

(10) Patent No.: US 6,417,395 B1
(45) Date of Patent: Jul. 9, 2002

(54) PROCESS FOR PREPARING METHIONINE

(75) Inventors: Hervé Ponceblanc, Villeurbanne; Olivier Favre-Bulle, Lyons; Georges Gros, Antony, all of (FR)

(73) Assignee: Aventis Animal Nutrition S.A., Antony (FR)

( * ) Notice: Subject to any disclaimer, the term of this patent is extended or adjusted under 35 U.S.C. 154(b) by 0 days.

(21) Appl. No.: 09/830,987

(22) PCT Filed: Oct. 29, 1999

(86) PCT No.: PCT/FR99/02650

§ 371 (c)(1),
(2), (4) Date: Jul. 12, 2001

(87) PCT Pub. No.: WO00/27809

PCT Pub. Date: May 18, 2000

(30) Foreign Application Priority Data

Nov. 6, 1998 (FR) .......................................... 98 14000

(51) Int. Cl.$^7$ ............................................. C07C 321/00

(52) U.S. Cl. ..................... 562/559; 562/557; 562/575; 562/570; 562/443; 562/444; 562/445

(58) Field of Search ............................... 562/559, 557, 562/575, 443, 444, 445, 570

(56) References Cited

FOREIGN PATENT DOCUMENTS

| EP | 084470 | * | 7/1983 |
| EP | 168282 | * | 1/1986 |

* cited by examiner

*Primary Examiner*—Paul J. Killos
*Assistant Examiner*—Hector M Reyes
(74) *Attorney, Agent, or Firm*—Connolly Bove Lodge and Hutz LLP

(57) ABSTRACT

The invention concerns a method for preparing methionine aminoamide. The invention also concerns the preparation of methionine without co-production of salts, from an aqueous solution containing essentially methionine aminonitrile by producing during a first step aminoamide followed by two complementary steps.

20 Claims, 1 Drawing Sheet

DESCRIPTIVE BLOCK DIAGRAM OF THE PROCESS ACCORDING TO THE INVENTION FOR PREPARING METHIONINE WITHOUT COPRODUCTION OF SALT

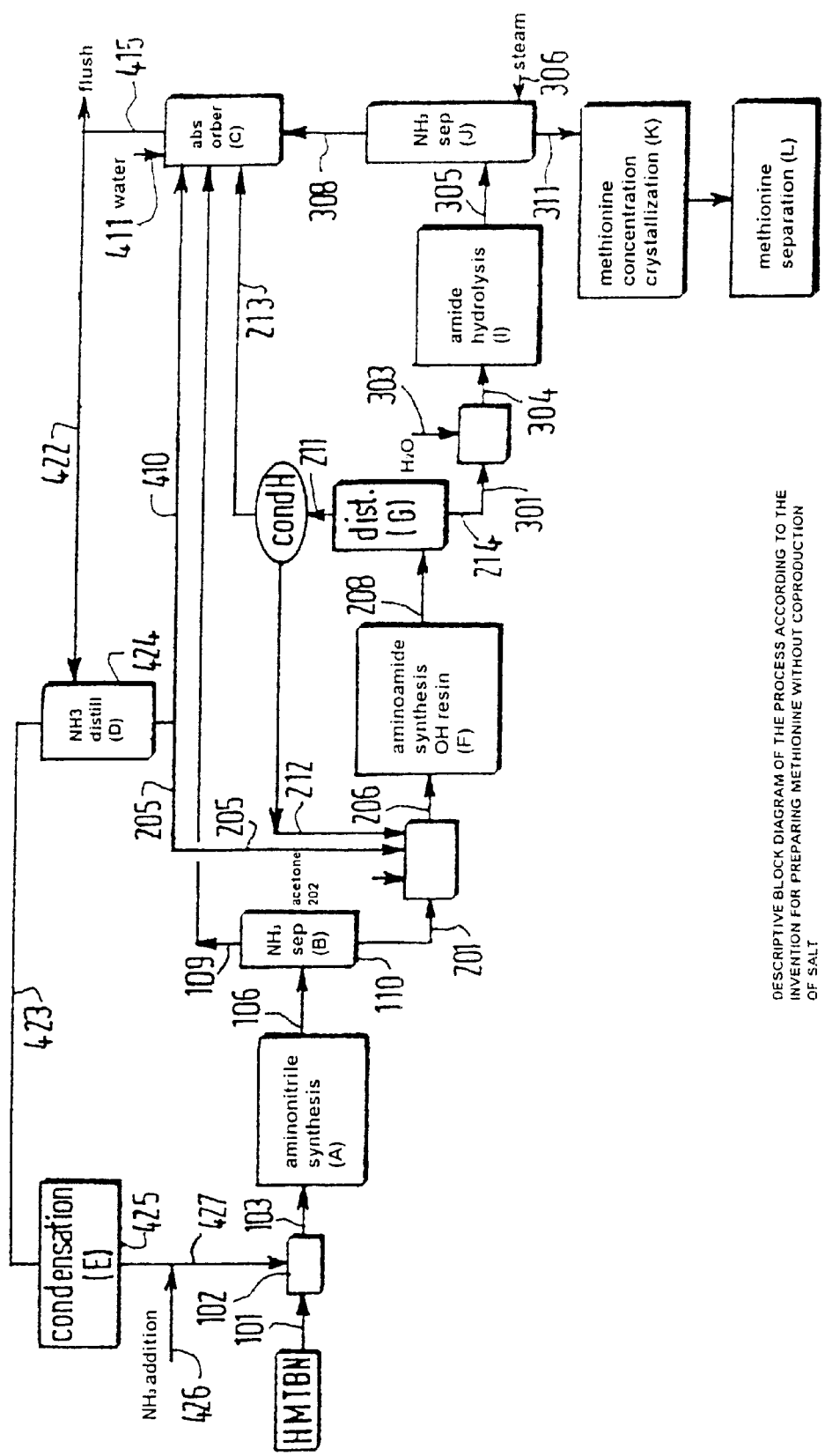
DESCRIPTIVE BLOCK DIAGRAM OF THE PROCESS ACCORDING TO THE INVENTION FOR PREPARING METHIONINE WITHOUT COPRODUCTION OF SALT

PROCESS FOR PREPARING METHIONINE

The present invention relates to a process for preparing methionine aminoamide. It also relates to the preparation of methionine without coproduction of sales, from an aqueous solution containing essentially methionine aminonitrile (or 2-amino-4-methylthiobutyronitrile, termed AMTBN), through the production, during a first step, of aminoamide, followed by two further steps.

The process for preparing methionine aminoamide (or 2-amino-4-methylthiobutyramide, termed ATMBM) consists in hydrating methionine aminonitrile in the presence of a catalyst of ketone type and of a basic resin of OH type. This hydration allows the production of a solution containing methionine aminoamide completely free of inorganic salts.

The process for preparing methionine consists of a process in three steps, the first of which is the step described above:

the aminonitrile is hydrated to methionine aminoamide in the presence of a catalyst of ketone type and of a basic resin of OH type, the methionine aminoamide is hydrolyzed to ammonium methioninate via various possible pathways:

via the chemical pathway by homogeneous catalysis, such as for example hydrolysis with aqueous ammonia, via the chemical pathway by heterogeneous catalysis, such as for example oxide-catalyzed hydrolysis, via the enzymatic pathway, finally, the methionine is recovered from the ammonium methioninate, after entrainment of the ammonia by stripping.

It is known, for example according to patent EP 84470 or EP 168282, that hydration of aminonitrile can be carried out on polymeric resin grafted with groups of ketone type (—(C=O)—), in the presence of hydroxide ions. The implementation of such a process, using a strong alkaline base (sodium hydroxide, potassium hydroxide, etc.) to supply the hydroxide ions required for catalysis, leads to the production of an aminoamide contaminated with the corresponding alkali.

In addition, it is known practice, for example according to patent EP 228938, to prepare methionine from methionine aminoamide using a strong base (for example, sodium hydroxide or another alkaline base) in order to carry out the alkaline hydrolysis of the amide. The implementation of such a process leads, during the acidification of the alkaline methioninate produced with a strong inorganic acid (sulfuric or hydrochloric acid), to the coproduction of an inorganic salt: the corresponding alkali metal sulfate or chloride.

In the two processes mentioned above, the use of a strong alkaline base as a catalyst for hydrating the aminonitrile and/or as a reagent for hydrolyzing the amide, leads to the coproduction of an inorganic salt: the corresponding alkali metal sulfate or chloride, which must then be separated from the methionine, often with great difficulty, using expensive processes of crystallization, filtration or successive concentration of the mother liquors.

The process according to the invention makes it possible to avoid the use of an alkaline base and, therefore, the coexistence, within the same flow, of methionine and of the inorganic salt, which must then be separated as described above.

Thus, the process according to the invention makes it possible to produce a flow of methionine free of inorganic salt.

The methionine aminonitrile (or 2-amino-4-methylthiobutyronitrile) can be produced by reacting aqueous ammonia on the corresponding cyanohydrin or any other means which would not bring salt into the medium.

Finally, the process according to the invention, for preparing the amide on hydroxide resin, makes it possible, during the contact with this resin, to eliminate the residual cyanides/nitriles which may exist at the end of the aminonitrile synthesis and which are harmful in the case of enzymatic hydrolysis of the aminoamide to ammonium methioninate, and also the presence of which is to be avoided in the final product.

For the catalyzed hydration of the aminonitrile to aminoamide, the resins are in particular chosen from basic hydroxide resins, such as the commercial resins sold under the trade names ROHM & HALS Ambersep 900 OH, or FLUKA.

After prolonged use, the resin is optionally regenerated by treatment in sodium-containing medium. The regeneration is preferably carried out with a sodium hydroxide solution according to a weight concentration of NaOH of at least 4% and according to an amount of NaOH of 80 to 150 g/liter of resin.

The present invention also relates to an industrial process for preparing methionine. According to this process, methylthiopropionic aldehyde is reacted with hydrocyanic acid in the presence of a basic catalyst or of a buffer allowing the pH of the solution to be maintained at between 5.5 and 7.5; among these catalysts, mention may be made of: tertiary amines, in particular triethylamine or pyridine, and citrate buffer. The hydrocyanic acid is used either pure or in a mixture with the gases derived from the synthesis thereof, such as nitrogen, carbon dioxide, carbon monoxide, water and methane, after, in particular, eliminating the ammonia. The reaction is preferably carried out at room temperature and in the presence of equimolar amounts of each of the reagents or of amounts of hydrocyanic acid which are slightly above the stoichiometry, such as, for example, according to an excess with respect to the stoichiometry of approximately 5%. The reaction can take place in a stirred reactor or in a tubular reactor; it can also take place in a gas-liquid contactor so as to allow reactive absorption, this being preferably when gaseous hydrocyanic acid is used.

At the end of the cyanation step, an aqueous solution of 2-hydroxy-4-methylthiobutyronitriles termed HMTBN (101), is obtained. This solution is brought into contact with ammonia (102) or with an ammonia/water mixture. The molar amount of ammonia used related to the HMTBN is advantageously between 4 and 7. The amounts specified hereinabove are described in patent DE 2645544. The ammonia is used pure or in aqueous solution. The aqueous solution of ammonia is preferably used at a concentration greater than 25% by weight, and preferably at a concentration greater than 60% by weight. Pure ammonia is most preferably used. The reaction temperature is preferably between 40 and 80° C., and most particularly between 55 and 70° C. The reaction is, in particular, carried out in a stirred or tubular flow reactor (A), in particular a plug-flow reactor. At the end of the reaction, an aqueous solution of 2-amino-4-methylthiobutyronitrile (106) is obtained.

At the end of the reaction, a portion of the excess ammonia is eliminated or separated by expansion of the simple flashtype or with entrainment using an inert gas such as, for example, nitrogen or steam, in a column (B). The temperature of the medium, during the separation step, is less than 60° C., and preferably between 15 and 50° C. The ammonia recovered (109), at the top of the column (B), is then absorbed in an absorber (C). The aqueous ammonia solution obtained (415/422) is then distilled (D). The gaseous ammonia obtained at the head of the distillation column (423) is condensed (E), and then, after optionally adding ammonia (426), is preferably reinjected in the form of a stream (427) into the aminonitrile synthesis reactor. The recycled ammonia stream (427) which is introduced into the aminonitrile synthesis reactor contains preferably less than 5% by weight of acetone.

The bottom (424) of the distillation column (D), containing water, acetone and ammonia, is divided into two streams (205) and (410). The lesser stream (205) is returned to the aminoamide synthesis and the greater stream (410) is sent to the absorber (C).

The aminonitrile contained in the stream (110) which is obtained at the bottom of the column (B) and which still contains in particular from 0.1 mol to 1.5 mol of residual ammonia per mole of aminonitrile is hydrated in the presence of a ketone (202 and 205), by contact with an ion-exchange resin of hydroxide type, in the reactor (F).

Among ketones, acetone is preferably used. The hydration of the aminonitrile is carried out in the presence of 0.1 to 1, preferably 0.2 to 0.6, acetone equivalents/mole of AMTBN. The hydration is carried out in particular in the presence of an amount of basic resin such that the number of hydroxide equivalents is, in particular, between 0.10 and 1, and preferably between 0.15 and 0.5, equivalent/mole of AMTBN. The reaction temperature is preferably set between 10 and 40° C., and even more preferably between 15 and 25° C. The reaction can be carried out continuously, discontinuously or semicontinuously, in a stirred or tubular reactor-type system or, finally, in a column containing the basic resin.

At the end of the reaction, an aqueous solution (208) containing the methionine aminoamide, aqueous ammonia, acetone, water and various organic compounds, such as, by way of nonlimiting indication, methionine or imidazolidinone, is obtained.

The mixture (208) obtained is, in particular, distilled in the column (G). The top of the column (211) is condensed in the condenser (H) so as to recover acetone containing little ammonia (212). This stream is recycled to the aminoamide synthesis. The uncondensable stream (213), containing essentially ammonia, is sent to the absorber (C).

The aqueous mixture (214) remaining in the bottom of the distillation column after elimination of the acetone, containing essentially the methionine aminoamide and the various organic compounds is then diluted (303) and then directed toward the aminoamide hydrolysis section (I).

This hydrolysis can be carried out via one of the following 3 pathways:

via the chemical pathway by homogeneous catalysis: hydrolysis with aqueous ammonia For better implementation of the invention, an $NH_3$/AMTBM molar ratio of between 2 and 25 mol/mole is preferably used. An AMTBM substrate concentration of preferably between 0.05 and 1 mol/kg is also used. With regard to the conditions of implementation of the invention, a temperature of between 100 and 180° C. is preferably used.

via the chemical pathway by heterogeneous catalysis

This hydrolysis is catalyzed, in particular, using one of the following oxides: $TiO_2$, $TiO_2/Al_2O_3$, $Nb_2O_5$, $Nb_2O_5$—$Al_2O_3$, ZnO and $ZrO_2$, and the heteropolyacids. The reaction is carried out preferably at the boiling point of the reaction mixture (approximately 100° C.), under atmospheric pressure and under continuous flushing of nitrogen so as to eliminate the ammonia formed. The AMTBM substrate concentration in the reaction medium is, according to a better embodiment of the invention, between 0.1 and 2 mol/kg and the catalyst/substrate mass ratio is between 0.5 and 1.5.

The latter pathway is particularly advantageous with respect to the processes described in patents JP 03093753, JP 03093754, JP 03093755 and JP 03093756 since:

it makes it possible to carry out the reaction at lower temperature and pressure, which makes it possible to avoid heat decomposition of the reagents and products, it makes it possible to recover acid methionine directly (while hot), without any other form of acidification and, therefore, without consuming inorganic acid. The separation of the solid catalyst and of the solubilized methionine while hot is easy.

via the enzymatic pathway using an amidase

This amidase is chosen from Rhodococcus IBN 20 or Brevibacterium R312 amidases. It is possible to use the genetic information encoding the amidase and to express it in a host microorganism. The host microorganism is, in particular, chosen from *Escherichia coli* or a member of the Corynebacterium genus. This biological material expressing the amidase activity is preferably immobilized.

The stream derived from the amide hydrolysis (305) is then treated, in the column (J), by entrainment using an inert gas (306), as chosen for example from nitrogen or steam, in a column, the temperature of which is regulated by the inlet streams of the various gases. In this column, the pressure is maintained preferably between $10^5$ and $2 \times 10^5$ Pa. At the top of the column (J), the ammonia and a portion of the water (308) are recovered, which are sent to the absorber (C).

The bottom of the column (J) containing an aqueous solution of methionine (311), free of ammonia, is concentrated (K) until a very concentrated slurry is obtained which can be vehicled to filtration or any other separation system (L) where it can be completely dried to the pulverulent state.

The following examples illustrate the implementation of the process according to the present invention.

EXAMPLE 1

HMTBN→AMTBN→AMTBM Sequence with Hydration of the AMTBN on Rohm and Haas Ambersep 900H Basic Resin and Degassing at 67° C. (Test AYP 031)

EX. 1.1

Preparation of the Methionine Aminonitrile 72 g of a Rectapur (30% w/w) commercial aqueous ammonia solution, namely 1270 mmol of $NH_3$, are loaded into a jacketed stainless steel autoclave reactor comprising baffles and magnetic stirring. After closing the reactor, the solution is heated to 67° C. via the jacket. The pressure stabilizes at 4 bar absolute.

42 g of a solution of HMTBN at 78.5% w/w in water, namely 251 mmol of HMTBN, are placed in a metal dropping funnel.

The content of the metal funnel is introduced rapidly into the autoclave under pressure, using a counter-pressure of 6 bar of nitrogen.

The mixture is then stirred for 15 minutes at 67° C. under 6 bar.

The medium is then immediately degassed at 67° C.

After opening the reactor, the medium having a final weight of 98.6 g is immediately transferred into an Erlenmeyer flask precooled to 10° C.

The experiment is repeated a second time using the same amounts. A second reaction medium of 100.4 g is then recovered.

The 2 reaction media are then mixed and stirred at 10° C., which produces an emulsion. The emulsion is then placed in a separating funnel.

An upper aqueous phase (pale yellow) of 165.7 g and a lower organic phase (dark yellow) of 31.7 g are then obtained.

The analysis by chromatography of the 2 phases makes it possible to assay:
177 mmol of 2-amino-4-methylthiobutyronitrile (AMTBN) in the organic phase,
295 mmol of AMTBN in the aqueous phase.

The total yield of recovery of the AMTBN with respect to the HMTBN introduced is 94%.

EX. 1.2
Preparation of the Methionine Aminoamide 60 g of Rohm and Haas Ambersep 900H basic resin at 1.5 OH milliequivalent/g (namely, 90 mmol of OH equivalent and, therefore, 0.19 mol of base/mole of AMTBN) and 65 g of water are loaded into a 1 l stirred glass reactor equipped with a Rushton turbine and baffles.

The suspension is stirred and maintained at 12° C.

The entire amount of the two phases obtained in example 1.1 (namely, 472 mmol of AMTBN) is used for this suspension, and also 13.9 g of acetone (namely, 239.6 mmol and, therefore, 0.51 mol of acetone/mole of AMTBN), with stirring at 500 rpm. The temperature of the mixture is brought to and maintained at 20° C.

After stirring for 2 h, chromatographic analysis shows that all of the AMTBN has reacted.

The medium is left for a total of 5 h with stirring, and then filtered. The filtrate is evaporated under vacuum at 45° C.

The yellow-colored viscous liquid obtained solidifies at room temperature in 30 min. A total weight of 61.9 g of this solid is then recovered.

NMR analysis of the solid obtained shows a molar purity of 96% aminoamide, 2% imidazolidinone, 0.5% methionine and 1.5% of various organic compounds.

Water analysis using the Karl-Fisher method gives a weight content of water of 1.4% on the solid recovered.

Chromatographic analysis of the same solid gives weight contents of 93% aminoamide, 3% imidazolidinone and 0.5% methionine, and various organic compounds.

The yields of recovery of the following products with respect to the AMTBN used in the second step are 82.3% for aminoamide, 2.1% for imidazolidinone and 0.4% for methionine.

EXAMPLE 2
HMTBN→AMTBN→AMTBM Sequence with Hydration of the AMTBN on Rohm and Haas Ambersep 900H Basic Resin and Degassing at 33° C. (Test AYP 035)

EX. 2.1
Preparation of the Methionine Aminonitrile 58.6 g of a solution of HMTBN at 78.8% w/w in water, namely 352 mmol of HMTBN, are loaded into a jacketed stainless steel autoclave reactor comprising baffles and magnetic stirring. After closing the reactor, the solution is heated to 51.5° C. via the jacket and a thermostated bath.

30.8 g of gaseous ammonia originating from a bottle (namely 1812 mmol of $NH_3$) are transferred into a metal dropping funnel maintained in dry ice and placed under vacuum beforehand.

The content of the metal funnel is introduced rapidly into the autoclave under pressure, using a counter-pressure of 10 bar of nitrogen.

The temperature of the stirred mixture stabilizes and is maintained at 67° C. using the thermostated bath. The mixture is stirred for 10 minutes under a pressure of 12 bar absolute.

The closed reactor is then cooled to 33° C. in 30 minutes, the pressure decreasing to 7 bar absolute, and then degassed.

After opening the reactor, the medium having a weight of 74.3 g is immediately cooled to 10° C. and placed in a separating funnel.

An upper aqueous phase (pale yellow) of 19.79 g and a lower organic phase (dark yellow) of 52.09 g are then obtained.

The analysis by chromatography of the 2 phases makes it possible to assay:
319.5 mmol of AMTBN in the organic phase,
32.6 mmol of AMTBN in the aqueous phase.

The total yield of recovery of the AMTBN with respect to the HMTBN introduced is 100%.

EX. 2.2
Preparation of the Methionine Aminoamide 41.9 g of Rohm and Haas Ambersep 900H basic resin at 1.5 OH mequivalent/g (namely, 62.9 mmol of OH equivalent) and 88.2 g of water are loaded into a 1 l stirred glass reactor equipped with a Rushton turbine and baffles.

The suspension is stirred and maintained at 15° C.

62.5 g of the mixture of the two phases obtained in example 2.1 (namely, 306 mmol of AMTBN) are used for this suspension, and also 9.2 g of acetone (namely, 158.6 mmol), with stirring at 360 rpm. The temperature of the mixture is brought to and maintained at 20° C. for 3 h.

The medium is then filtered. The filtrate is evaporated under vacuum (1 mm of Hg) at 30° C.

The yellow-colored viscous liquid obtained solidifies at room temperature. A total weight of 43.8 g of this solid is then recovered.

Chromatographic analysis of the same solid gives weight contents of 78% aminoamide, 11% imidazolidinone and 3% methionine, and various organic compounds.

The yields of recovery of the following products with respect to the AMTBN used in the second step are 75.3% for aminoamide, 10.6% for imidazolidinone and 2.9% for methionine.

EXAMPLE 3
AMTBM Hydrolysis with Aqueous Ammonia (Test AYP 036)

52 g of a Rectapur (30% w/w) commercial aqueous ammonia solution, namely 918 mmol of $NH_3$, are loaded into a jacketed stainless steel autoclave reactor comprising baffles and magnetic stirring. After closing the reactor, the solution is heated to 134° C. via the jacket, with stirring.

27.2 g of a solution of AMTBM at 1.4 mol/kg, produced by mixing 7.3 g of the aminoamide prepared in example 2.2 (namely 38.4 mmol of AMTBM) and 19.9 g of water, are placed in a metal dropping funnel.

The content of the metal funnel is introduced rapidly into the autoclave under pressure, using a counter-pressure of 20 bar of nitrogen. The mixture thus produced is at 0.49 mol/kg for AMTBM. It is then stirred at 150° C., under pressure.

After reacting for 1 h 30, a methionine yield of 53% (taken with respect to the starting imidazolidinone and AMTBM) is obtained.

After reacting for 7 h, a methionine yield of 81% is thus obtained.

EXAMPLE 4
AMTBM Hydrolysis with Aqueous Ammonia (Test AYP 038)

In this example, the same procedure as in example 3 above is followed, using:
88.8 g of a mixture consisting of 22.8 g of a Rectapur (30% w/w) commercial aqueous ammonia solution, namely 402 mmol of $NH_3$, and of 66.0 g of water, 23.7 g of a solution of AMTBM at 0.7 mol/kg, produced by mixing 3.2 g of the aminoamide prepared in example 2.2 (namely 16.8 mmol of AMTBM) and 20.5 g of water. The mixture obtained is at 0.15 mol/kg for AMTBM.

After reacting for 1 h 30 at 150° C., a methionine yield of 72% (taken with respect to the starting imidazolidinone and AMTBM) is obtained.

Alter reacting for 7 h, a quantitative methionine yield is thus obtained.

EXAMPLE 5
AMTBM Hydrolysis on a $TiO_2$ Catalyst (Test ASE 065)

66.2 g of water and 7.98 g of pre-ground $TiO_2$ catalyst are loaded into a jacketed glass reactor. The only outlet of the reactor is connected to a series of bubblers containing diluted sulfuric acid (2% w/w).

The suspension contained in the reactor is stirred and heated to 94° C., under a flow of nitrogen.

An aqueous solution of AMTBM at 1.35 mol/kg, produced by mixing 10 g of crude aminoamide of example 2.2 (namely 52.6 mmol of AMTBM) and 29.02 g water, is introduced into the reactor by means of a pump The solution thus obtained in the reactor is at 0.5 mmol/kg of AMTBM.

After reacting for 30 minutes, the aminoamide conversion is complete. The methionine yield obtained is 85%.

EXAMPLE 6
AMTBM Hydrolysis on a $TiO_2/Al_2O_3$ Catalyst (Test ASE 064)

In this example, the same procedure as in example 5 above is followed, using:

8.0 g of $TiO_2/Al_2O_3$ catalyst at 3% by weight of Ti,
10.94 g of crude amide of example 2.2 (namely 57.6 mmol of AMTBM) and a total of 92.7 g of water.

The solution thus obtained in the reactor is at 0.56 mol/kg of AMTBM.

After reacting for 7 hours, the aminoamide conversion is approximately 52%. The methionine yield obtained is approximately 30%.

EXAMPLE 7
Enzymatic Hydrolysis of the AMTBM Using *Corynebacterium Glutamicum* pYG822 (Tests GF571 and 590)

The *corynebacterium glutamicun* strain pYG822, described in French patent No. 9014853 (Nov. 28, 1990), expresses the Rhodococcus IBN 20 amidase. The corynebacterium is cultured for 24 hours at 30° C. in 1 liter of medium containing 10 g of tryptone, 5 g of yeast extract, 5 g of NaCl and 20 mg of kanamycin. The cell pellet is recovered by centrifugation. The cell pellet, 0.1 liter of 100 mM phosphate buffer, pH 7.0, and 2.2 g of AMTBM originating from example 2.2 are loaded into a reactor. After reacting for 6 hours at 35° C., the aminoamide conversion is 100%. The methionine yield is 100%.

EXAMPLE 8
Enzymatic Hydrolysis of the AMTBM Using *Escherichia coli* pXL1751 (Test GF584)

The *Escherichia coli* strain pXL1751, described in European patent No. 433 117(91-179908B), expresses the Brevibacterium R312 amidase. The *E. coli* is cultured for 24 hours at 37° C. in 1 liter of M9 medium (DIFCO) containing 4 g of Casamino acids, 5 g of yeast extract and 100 mg of ampicillin. The cell pellet is recovered by centrifugation. The cell pellet, 0.1 liter of 100 mM phosphate buffer, pH 7.0, and 2.2 g of AMTBM originating from example 2.2 are loaded into a reactor. After reacting for 6 hours at 35° C., the aminoamide conversion is 100%. The methionine yield is 100%.

Counter-example 1
AMTBM Hydrolysis on $Al_2O_3$ (Test ASE 063)

In this example, the same procedure as in example 5 above is followed, using:

8.4 g of $Al_2O_3$ catalyst as beads,
10.95 g of crude amide of example 2.2 (namely 57.6 mmol of AMTBM) and a total of 108 g of water.

The solution thus obtained in the reactor is at 0.48 mol/kg of AMTBM.

After reacting for 7 hours, the aminoamide conversion and the methionine yield are practially zero.

What is claimed is:

1. Process for preparing methionine aminoamide (or 2-amino-4-methylthiobutyramide), characterized in that methionine aminonitrile is hydrated in the presence of a catalyst of ketone type and of a basic resin of hydroxide type.

2. Process according to claim 1, characterized in that the ketone used is acetone.

3. Process according to claim 1, characterized in that the molar amount of acetone used with respect to the aminonitrile is from 0.2 to 0.6 acetone equivalents/mole of aminonitrile.

4. Process according to claim 1, characterized in that the amount of basic resin used with respect to the aminonitrile is from 0.10 to 1 hydroxide equivalents/mole of aminonitrile.

5. Process according to claim 1, characterized in that the reaction temperature is from 10 to 40° C.

6. Process according to claim 1, characterized in that the reaction is carried out continuously, discontinuously or semicontinuously.

7. Process for preparing methionine, characterized in that, in a first step, methionine aminonitrile is hydrated to methionine aminoamide in the presence of a catalyst of ketone type and of a basic resin of OH type, in a second step, the methionine aminoamide is hydrolyzed to ammonium methioninate, via the chemical pathway by homogeneous catalysis, via the chemical pathway by heterogeneous catalysis or via the enzymatic pathway and, in a third step, the methionine is recovered, from the ammonium methioninate after elimination of the ammonia.

8. Process according to claim 7, characterized in that the methionine aminoamide hydrolysis is carried out via the chemical pathway by homogeneous catalysis in the presence of aqueous ammonia.

9. Process according to claim 7, characterized in that the methionine aminoamide hydrolysis is carried out via the chemical pathway by heterogeneous catalysis in the presence of metal oxides or of heteropolyacids.

10. Process according to claim 9, characterized in that the metal oxides are selected from the group consisting of $TiO_2$, $TiO_2/Al_2O_3$, $Nb_2O_5$, $Nb_2O_5$—$Al_2O_3$, ZnO and $ZrO_2$.

11. Process according to claim 7, characterized in that the methionine aminoamide hydrolysis is carried out via the enzymatic pathway in the presence of an amidase.

12. Process according to claim 11, characterized in that the amidase is derived from Rhodococcus or Brevibacterium microorganisms.

13. Process according to claim 11, characterized in that use is made of genetic information encoding an amidase, which is expressed in a host microorganism.

14. Process according to claim 13, characterized in that the host microorganism is chosen from *Escherichia coli* or a member of the corynebacterium genus.

15. Process according to claim 14 , characterized in that the host microorganism expressing the amidase activity is immobilized.

16. Process according to claim 1, characterized in that the amount of basic resin used with respect to the aminonitrile is from 0.15 to 0.5 hydroxide equivalents/mole of aminonitrile.

17. Process according to claim 1, characterized in that the reaction temperature is from 15 to 25° C.

18. Process for preparing 2-amino-4-methylthiobutyramide, comprising the step of hydrating 2-amino-4-methylthiobutyronitrile in the presence of a catalyst of ketone type and of a basic resin of hydroxide type, wherein said process does not produce any inorganic salts.

19. Process of claim 18, wherein said catalyst of ketone type consists essentially of acetone and the molar amount of acetone used with respect to the 2-amino-4-methylthiobutyronitrile is from 0.1 to 1 acetone equivalents/mole of 2-amino-4-methylthiobutyronitrile.

20. Process of claim 18, wherein the amount of basic resin used with respect to the 2-amino-4-methylthiobutyronitrile is from 0.10 to 1 hydroxide equivalents/mole of 2-amino-4-methylthiobutyronitrile.

* * * * *